US009057678B2

(12) United States Patent
Lee et al.

(10) Patent No.: US 9,057,678 B2
(45) Date of Patent: Jun. 16, 2015

(54) IMAGE RECONSTRUCTION SYSTEM, APPARATUS, AND METHOD EMPLOYING NON-SEQUENTIAL SCANNING SCHEME USING REAL-TIME FEEDBACK

(71) Applicant: Samsung Electronics Co., Ltd., Suwon-si (KR)

(72) Inventors: Jae Hak Lee, Yongin-si (KR); Jong Ha Lee, Hwaseong-si (KR); Sung Cheol Kim, Goyang-si (KR); Young Hun Sung, Hwaseong-si (KR); Kang Eui Lee, Yongin-si (KR); Kwang Eun Jang, Busan (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 238 days.

(21) Appl. No.: 13/679,787

(22) Filed: Nov. 16, 2012

(65) Prior Publication Data
US 2013/0195241 A1 Aug. 1, 2013

(30) Foreign Application Priority Data

Jan. 26, 2012 (KR) ........................ 10-2012-0007649

(51) Int. Cl.
*G01N 23/04* (2006.01)
(52) U.S. Cl.
CPC .............. *G01N 23/04* (2013.01); *G01N 23/046* (2013.01); *G01N 2223/419* (2013.01)
(58) Field of Classification Search
USPC ...................................................... 378/1, 41
See application file for complete search history.

(56) References Cited

U.S. PATENT DOCUMENTS

| 5,812,629 | A | 9/1998 | Clauser |
| 6,118,841 | A | 9/2000 | Lai |
| 6,469,717 | B1 | 10/2002 | Winkeke et al. |
| 2008/0256494 | A1 | 10/2008 | Greenfield |
| 2011/0222758 | A1* | 9/2011 | Kanagawa et al. ........... 382/154 |

FOREIGN PATENT DOCUMENTS

| JP | 2009-28160 A | 2/2009 |
| JP | 2010-165109 A | 7/2010 |
| KR | 10-2000-0053872 A | 9/2000 |
| KR | 10-2006-0085596 A | 7/2006 |

* cited by examiner

*Primary Examiner* — Nicole Ippolito
*Assistant Examiner* — Hanway Chang
(74) *Attorney, Agent, or Firm* — NSIP Law

(57) ABSTRACT

An image reconstruction system, apparatus, and method employing a non-sequential scanning scheme using real-time feedback are provided. A projection information generating unit is configured to generate at least one piece of projection information by the X-ray irradiated to the object in the at least one viewpoint. A projection information comparing unit is configured to compare predicted intermediate projection information with measured intermediate projection information from the generated projection information. The predicted intermediate projection information is predicted from pieces of projection information generated from different viewpoints, and the measured intermediate projection information is measured in an intermediate viewpoint corresponding to the predicted intermediate projection information. A determining unit is configured to determine whether to irradiate the X-ray to the object in an additional viewpoint. An image reconstructing unit is configured to reconstruct the generated projection information, and to acquire an image representing the object.

22 Claims, 4 Drawing Sheets

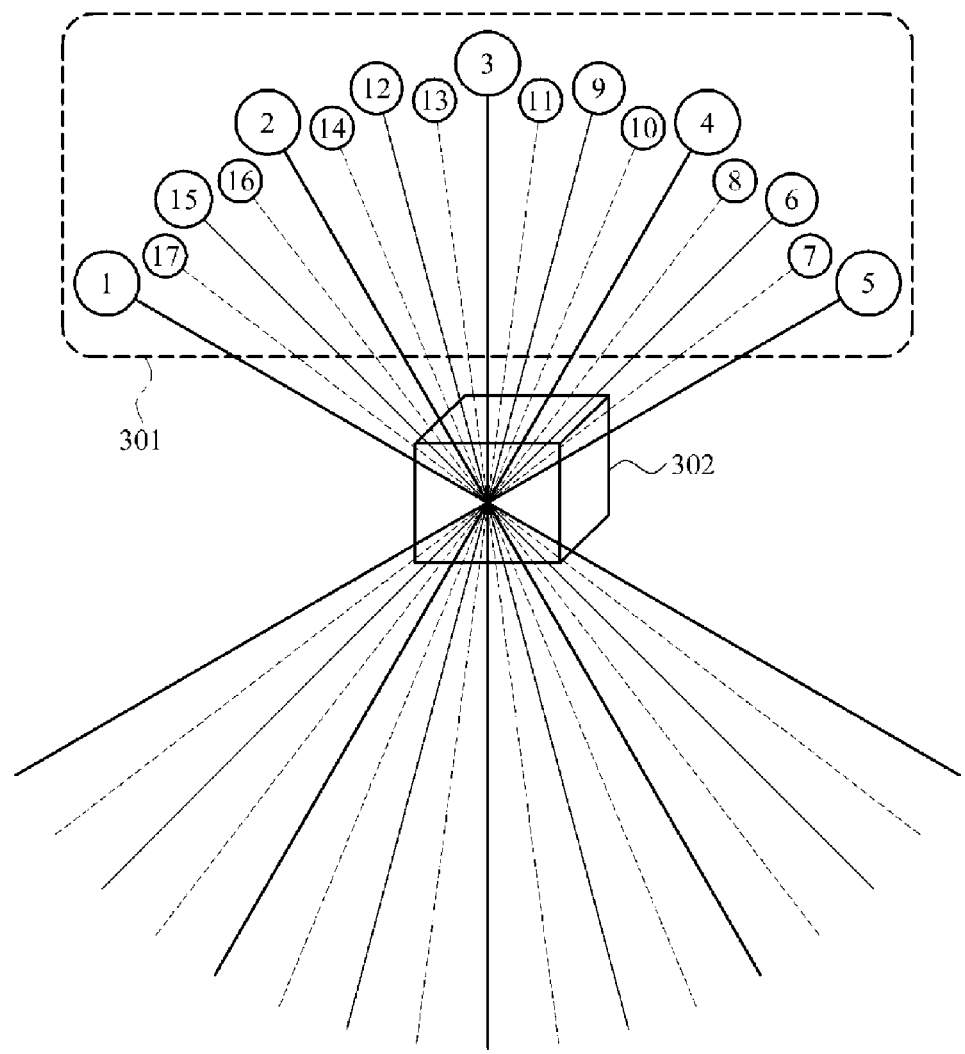

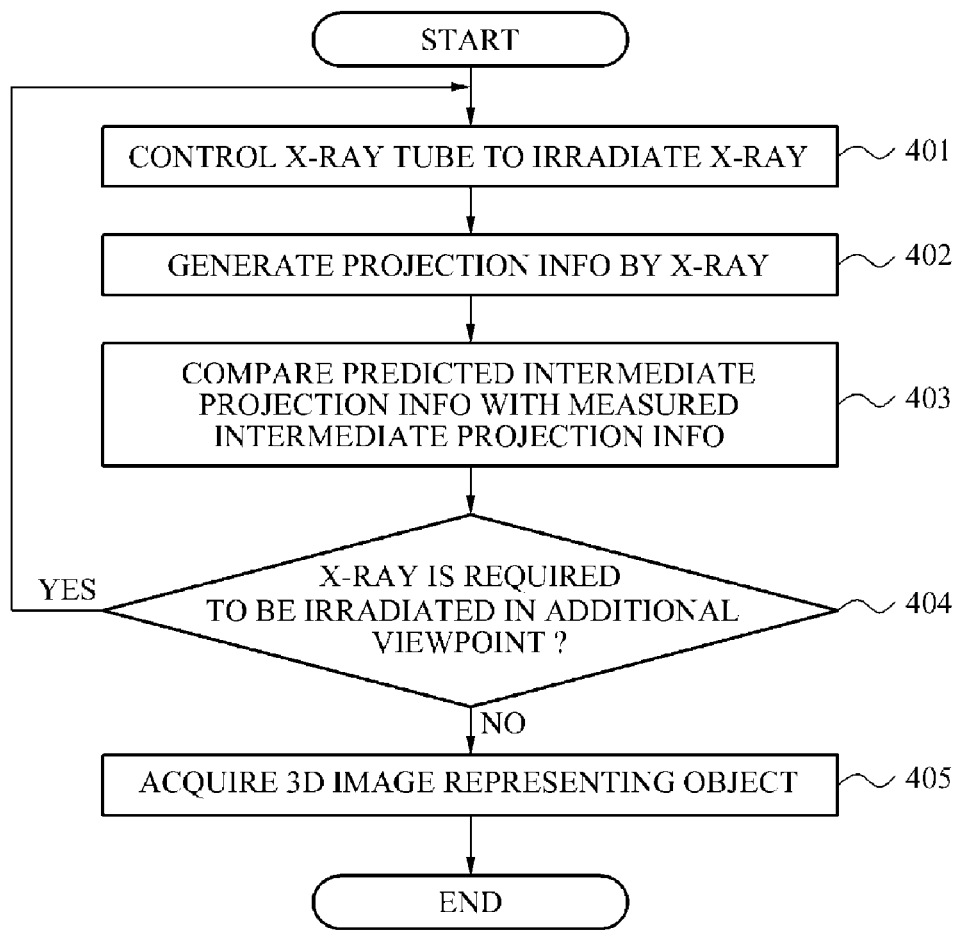

IMAGE RECONSTRUCTION SYSTEM, APPARATUS, AND METHOD EMPLOYING NON-SEQUENTIAL SCANNING SCHEME USING REAL-TIME FEEDBACK

CROSS-REFERENCE TO RELATED APPLICATION(S)

This application claims the benefit under 35 U.S.C. §119 (a) of Korean Patent Application No. 10-2012-0007649, filed on Jan. 26, 2012, in the Korean Intellectual Property Office, the entire disclosure of which is incorporated herein by reference for all purposes.

BACKGROUND

1. Field

The following description relates to an image reconstruction system and method employing a non-sequential scanning scheme using real-time feedback, and relates to a non-sequential scanning scheme using real-time feedback information.

2. Description of Related Art

Tomosynthesis, also digital tomosynthesis, is a method for performing high-resolution limited-angle tomography at mammographic dose levels.

In an example of a general tomosynthesis system, when a scan range of −30° to +30° and an interval of 3° are set, a total of 21 views may be acquired sequentially from −30° to +30° at intervals of 3°.

Subsequently, the tomosynthesis system may perform image reconstruction using the acquired views and may acquire three-dimensional (3D) information.

In this example, as the scan range becomes wider and as an interval between views becomes smaller, an improved reconstruction result may be obtained. There is a limit to the detail and accuracy of the reconstruction result due to a limit in a dose and range of an X-ray. The tomosynthesis system is unable to offer the extremely narrow slice widths. To overcome these limitations, major medical device companies set their own scan ranges and intervals, and set system system specifications to minimize a dose of an X-ray to obtain a best reconstruction result within the set scan ranges and the set intervals.

FIG. 1 illustrates an example of a sequential scanning scheme. The sequential scanning scheme of FIG. 1 may be used in an existing medical system. In the existing medical system, an X-ray tube 101 irradiates an X-ray to an object 102 while moving from a viewpoint 1 to a viewpoint 17, and acquires projection information. In the sequential scanning scheme, projection information is obtained unconditionally based on a scan range and an interval that are pre-set.

SUMMARY

In accordance with an illustrative configuration, an image reconstruction system employing a non-sequential scanning scheme includes a projection information generating unit configured to generate a piece of projection information by an X-ray irradiated to an object in a viewpoint. The image reconstruction system further includes a projection information comparing unit configured to compare predicted intermediate projection information with measured intermediate projection information from the generated projection information. The predicted intermediate projection information is predicted from pieces of projection information generated from different viewpoints, and the measured intermediate projection information is measured in an intermediate viewpoint corresponding to the predicted intermediate projection information. The image reconstruction system also includes a determining unit configured to determine whether to irradiate the X-ray to the object in an additional viewpoint based on a result of the comparing. The image reconstruction system includes an image reconstructing unit configured to reconstruct the generated projection information, and to acquire an image representing the object.

The projection information generating unit is further configured to generate first projection information based on an X-ray irradiated in a first viewpoint, and to generate second projection information based on an X-ray irradiated in a second viewpoint.

The projection information comparing unit is further configured to compare predicted intermediate projection information predicted from the first projection information and the second projection information, with measured intermediate projection information measured in an intermediate viewpoint, which corresponds to the predicted intermediate projection information.

The projection information generating unit is further configured to interpolate the first projection information and the second projection information, and to generate the predicted intermediate projection information.

The image reconstruction system further includes an X-ray irradiator configured to control an X-ray tube to irradiate the X-ray to the object in the viewpoint. When a difference between the predicted intermediate projection information and the measured intermediate projection information is greater than a predetermined reference, the X-ray irradiating unit is further configured to control the X-ray to be irradiated in the additional viewpoint to generate additional projection information.

When a difference between the predicted intermediate projection information and the measured intermediate projection information is equal to or less than a predetermined reference as the result of the comparing, the projection information generator is further configured to generate first additional projection information by interpolating the measured intermediate projection information and the first projection information, and to generate second additional projection information by interpolating the measured intermediate projection information and the second projection information. The image reconstructing unit is a three-dimensional (3D) image reconstructing unit.

In accordance with another illustrative configuration, there is provided an image reconstruction method using a non-sequential scanning scheme. The image reconstruction method includes generating at least one piece of projection information by an X-ray irradiated to an object in a viewpoint. The image reconstruction method includes comparing predicted intermediate projection information with measured intermediate projection information from the generated projection information. The predicted intermediate projection information is predicted from pieces of projection information generated from different viewpoints, and the measured intermediate projection information is measured in an intermediate viewpoint corresponding to the predicted intermediate projection information. The image reconstruction method includes determining whether to irradiate the X-ray to the object in an additional viewpoint based on a result of the comparing. The image reconstruction method further includes reconstructing the generated projection information, and acquiring an image representing the object. The generating further includes generating first projection information based on an X-ray irradiated in a first viewpoint, and generating second projection information based on an X-ray irradiated in a second viewpoint.

The comparing further includes comparing predicted intermediate projection information predicted from the first projection information and the second projection information, with measured intermediate projection information measured in an intermediate viewpoint corresponding to the predicted intermediate projection information.

The generating further includes interpolating the first projection information and the second projection information, and generating the predicted intermediate projection information.

The controlling further includes controlling the X-ray to be irradiated in the additional viewpoint so that additional projection information is generated, when a difference between the predicted intermediate projection information and the measured intermediate projection information is greater than a predetermined reference.

In addition, in accordance with an illustrative example, a computer program embodied on a non-transitory computer readable recording medium, the computer program is configured to control a processor to perform the image reconstruction method described above.

In accordance with an alternative illustrative example, an image reconstruction apparatus using a non-sequential scanning scheme includes a projection information generator configured to generate a piece of projection information using an X-ray irradiated to an object in a viewpoint. The image reconstruction apparatus includes a projection information comparator configured to compare predicted intermediate projection information and measured intermediate projection information from the generated projection information and outputting a result indicative thereof. The image reconstruction apparatus includes a determining processor configured to control the X-ray to be irradiated in an additional viewpoint to generate additional projection information when a difference between the predicted intermediate projection information and the measured intermediate projection information is greater than a predetermined reference. The image reconstruction apparatus further includes an image processor configured to reconstruct the generated projection information to produce an image of the object.

The predicted intermediate projection information is predicted from pieces of projection information generated from different viewpoints, and the measured intermediate projection information is measured in an intermediate viewpoint corresponding to the predicted intermediate projection information.

The image reconstruction apparatus also includes an X-ray irradiator configured to control an X-ray tube to irradiate the X-ray to the object in the viewpoint. When a difference between the predicted intermediate projection information and the measured intermediate projection information is greater than a predetermined reference, the X-ray irradiating unit is further configured to control the X-ray to be irradiated in the additional viewpoint to generate additional projection information.

When a difference between the predicted intermediate projection information and the measured intermediate projection information is equal to or less than a predetermined reference as the result of the comparing, the projection information generator is further configured to generate first additional projection information by interpolating the measured intermediate projection information and a first projection information, and to generate second additional projection information by interpolating the measured intermediate projection information and a second projection information.

In accordance with an illustrative example, an image reconstruction method using a non-sequential scanning scheme includes generating a piece of projection information using an X-ray irradiated to an object in a viewpoint. The image reconstruction method also includes comparing predicted intermediate projection information and measured intermediate projection information from the generated projection information and outputting a result indicative thereof. The image reconstruction method also includes controlling the X-ray to be irradiated in an additional viewpoint to generate additional projection information when a difference between the predicted intermediate projection information and the measured intermediate projection information is greater than a predetermined reference. The image reconstruction method also includes reconstructing the generated projection information to produce an image of the object.

The comparing further includes comparing predicted intermediate projection information predicted from the first projection information and the second projection information, with measured intermediate projection information measured in an intermediate viewpoint corresponding to the predicted intermediate projection information.

The generating further includes interpolating the first projection information and the second projection information, and generating the predicted intermediate projection information.

The controlling further includes controlling the X-ray to be irradiated in the additional viewpoint so that additional projection information is generated, when a difference between the predicted intermediate projection information and the measured intermediate projection information is greater than a predetermined reference.

In addition, in accordance with an illustrative example, a computer program embodied on a non-transitory computer readable recording medium, the computer program is configured to control a processor to perform the image reconstruction method described above.

Other features and aspects will be apparent from the following detailed description, the drawings, and the claims.

BRIEF DESCRIPTION OF THE DRAWINGS

FIG. 3 is a diagram illustrating an example of an operation of the image reconstruction system of FIG. 2.

FIG. 4 is a flowchart illustrating an example of an image reconstruction method using a non-sequential scanning scheme.

Figure 1:
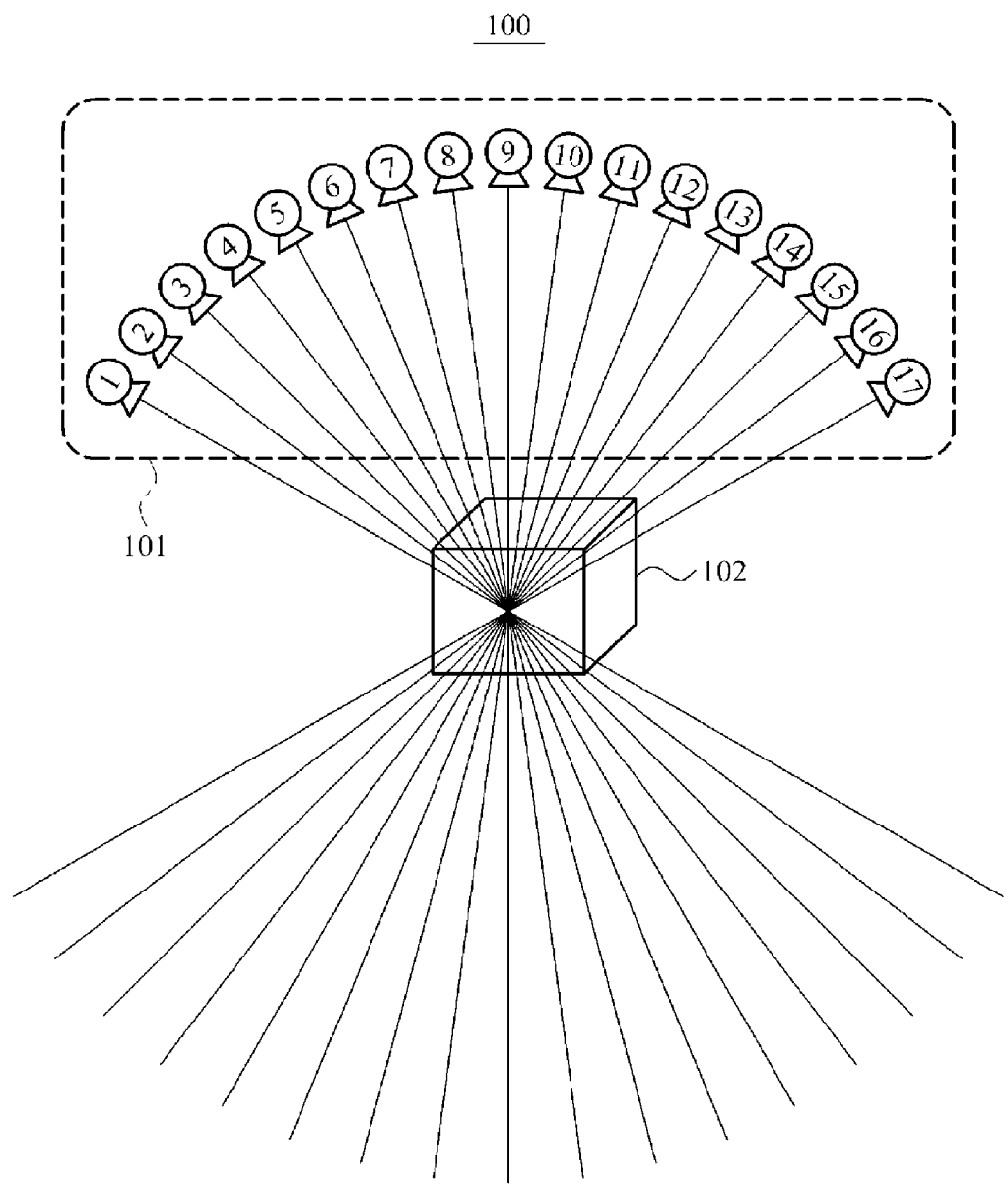
FIG. 1 is a diagram illustrating an example of a sequential scanning scheme.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, description of well-known functions and constructions may be omitted for increased clarity and conciseness.

Figure 2:
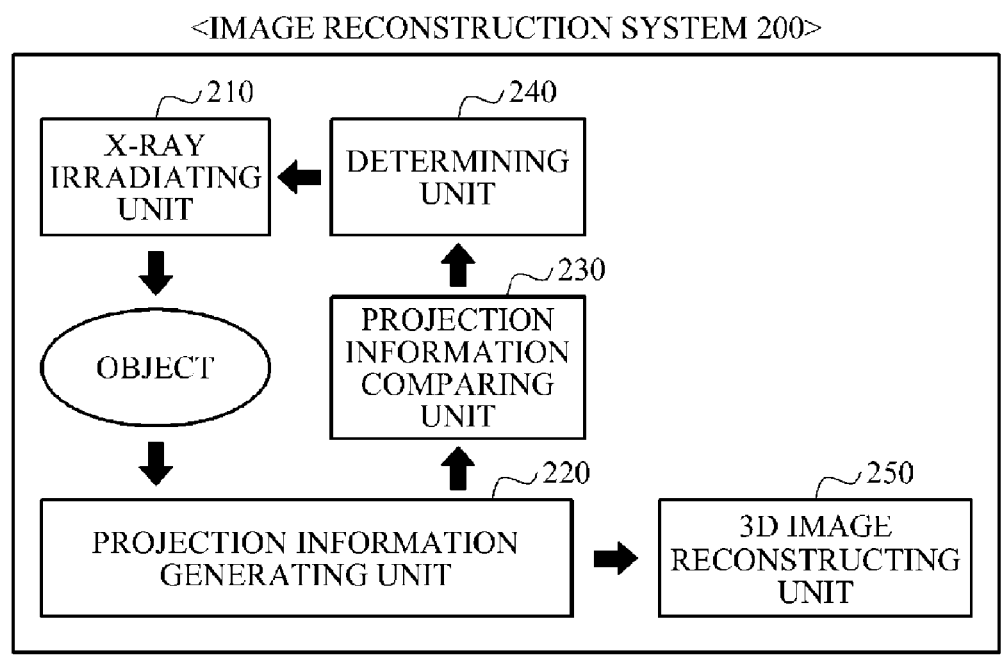
FIG. 2 is a block diagram illustrating an example of an image reconstruction system employing a non-sequential scanning scheme.

FIG. 2 illustrates an image reconstruction system 200 employing a non-sequential scanning scheme, in accordance with an illustrative configuration. According to embodiments, relationship information may be used, which are associated with a relationship between pieces of neighboring projection information acquired through real-time scanning. The relationship information may be provided as feedback to a system reconstruction system 200 and to set a next scan path.

The relationship information may be obtained by measuring, in real time, a correlation value between an intermediate view generated using the neighboring projection information and a viewpoint for the intermediate view. For example, when a high correlation value is obtained, the intermediate view has a high reliability. Accordingly, a view of an intermediate area may be used to reconstruct an image using an intermediate view generated in software manner, without a need to be further scanned. In other words, a view of a corresponding intermediate area may move to a next scan path, rather than being scanned. Thus, a dose of an X-ray may be reduced.

The above scheme is based on the premise that unconditionally densely scanning may be unnecessary, depending on a structure of an object.

Referring to FIG. 2, the image reconstruction system 200 includes an X-ray irradiating unit or X-ray irradiator 210, a projection information generating unit or projector information generator 220, a projection information comparing unit or projection information comparator 230, a determining unit or determining processor 240, and a three-dimensional (3D) image reconstructing unit or three-dimensional (3D) processor 250. In one illustrative example, structurally, each of the X-ray irradiating unit or X-ray irradiator 210, the projection information generating unit or projector information generator 220, the projection information comparing unit or projection information comparator 230, the determining unit or determining processor 240, and the three-dimensional (3D) image reconstructing unit or three-dimensional (3D) processor 250 is an assembly, application specific, integrated circuit (ASIC), controller or processor enable to operate or function independently and/or in combination with other structural elements illustrated in FIG. 2.

The X-ray irradiating unit 210 controls an X-ray tube to irradiate an X-ray to an object in at least one viewpoint.

The projection information generating unit 220 generates at least one piece of projection information by the X-ray irradiated to the object in the at least one viewpoint. For example, the projection information generating unit 220 generates first projection information based on an X-ray irradiated in a first viewpoint among the at least one viewpoint, and generates second projection information based on an X-ray irradiated in a second viewpoint among the at least one viewpoint.

The projection information comparing unit 230 compares predicted intermediate projection information, with measured intermediate projection information, among the generated projection information. The predicted intermediate projection information may be predicted from pieces of projection information generated from different viewpoints, and the measured intermediate projection information may be measured in an intermediate viewpoint corresponding to the predicted intermediate projection information. In one example, the projection information comparing unit 230 may compare predicted intermediate projection information with measured intermediate projection information. The predicted intermediate projection information is predicted from the first projection information and the second projection information. The measured intermediate projection information is measured in an intermediate viewpoint corresponding to the predicted intermediate projection information. In this example, the projection information generating unit 220 generates the predicted intermediate projection information by interpolating the first projection information and the second projection information.

In addition, the projection information comparing unit 230 compares the predicted intermediate projection information with the measured intermediate projection information and outputs a result indicative thereof. The determining unit 240 determines whether to irradiate the X-ray to the object in an additional viewpoint by controlling the X-ray tube and based on the result of the comparing. For example, when the projection information comparing unit 230 determines that a difference between the predicted intermediate projection information and the measured intermediate projection information is greater than a predetermined reference, that is, when a correlation value is equal to or less than a predetermined value, the determining unit 240 controls the X-ray irradiating unit 210 to more finely, precisely, or accurately generate projection information.

In other words, the X-ray irradiating unit 210 irradiates the X-ray in the additional viewpoint, and controls the projection information generating unit 220 to generate additional projection information. The X-ray irradiating unit 210 determines that a correlation value between pieces of neighboring projection information to be low, and irradiates the X-ray in a corresponding viewpoint so that projection information corresponding to an intermediate area between the pieces of neighboring projection information may be additionally generated. The 3D image reconstructing unit 250 reconstructs the generated projection information, and acquires a 3D image representing the object.

FIG. 3 illustrates an example of an operation of the image reconstruction system 200 of FIG. 2. As illustrated in FIG. 3, instead of setting a scan path in a sequence of viewpoints at regular intervals with respect to the X-ray tube 301, an image reconstruction system 300 employing a non-sequential scanning scheme sets, non-sequentially in advance, an expected scan path. The expected scan path may be set using various schemes other than the scheme of FIG. 3. For example, the image reconstruction system 300 controls an X-ray tube 301 to irradiate an X-ray to an object 302 in a sequence of viewpoints 1 through 5. The image reconstruction system 300 then controls an X-ray tube 301 to generate projection information in each of the viewpoints 1 through 5. Additionally, when projection information is acquired in the viewpoint 5, the image reconstruction system 300 determines, as an intermediate viewpoint, a viewpoint 6 that may include an intermediate point between the viewpoints 4 and 5.

The image reconstruction system 300 generates predicted intermediate projection information that is predicted from first projection information acquired in the viewpoint 4 and second projection information acquired in the viewpoint 5.

In this example, the image reconstruction system 300 interpolates the first projection information and the second projection information, and generates the predicted intermediate projection information.

Subsequently, the image reconstruction system 300 measures projection information by irradiating the X-ray in an intermediate viewpoint, where the predicted intermediate projection information is generated. The measured projection information may be processed as measured intermediate projection information.

The image reconstruction system 300 compares the predicted intermediate projection information corresponding to the viewpoint 6 with the measured intermediate projection information. The image reconstruction system 300 also verifies a correlation value between the predicted intermediate projection information and the measured intermediate projection information.

Additionally, the image reconstruction system 300 determines whether to measure or predict prediction information corresponding to additional viewpoints, for example, viewpoints 7 and 8, based on the correlation value. In one example, when the predicted intermediate projection information and the measured projection information are determined to have a high similarity, the image reconstruction system 300 determines that there is no need to actually irradiate an X-ray in the viewpoints 7 and 8 and to perform scanning Instead, the image reconstruction system 300 predicts projection information corresponding to the viewpoint 7 using projection information corresponding to the viewpoints 5 and 6, which are already scanned. The image reconstruction system 300 predicts projection information corresponding to the viewpoint 8 using projection information corresponding to the viewpoints 4 and 6. The image reconstruction system 300 uses the predicted projection information to reconstruct an image.

Because there is no need to irradiate an X-ray to measure projection information corresponding to the viewpoints 7 and 8, a dose of the X-ray may be reduced. Accordingly, the image reconstruction system 300 may be applied to various medical systems that acquire X-ray multi-views and reconstruct an image using the acquired X-ray multi-views. As a result, the image reconstruction system 300 makes it possible to expect an effect of reducing a dose of the X-ray.

The image reconstruction system 300 may be applied to a medical image reconstruction system and method using X-ray multi-views, for example, an X-ray reconstruction field. The image reconstruction system 300 may be also applied to a tomosynthesis field, or a computed tomography (CT) reconstruction field in which projection information is acquired sequentially based on a given scan range and a given interval, and in which reconstruction is performed. For example, when the image reconstruction system 300 is applied to a tomosynthesis field, or a CT reconstruction field, a view that does not need to be scanned may be automatically determined, and automatically excluded.

Accordingly, it is possible to obtain an effect of reducing a dose of the X-ray, by analyzing, in real time, information overlapping between neighboring views, and by selecting only a view required for reconstruction.

FIG. 4 illustrates an example of an image reconstruction method using a non-sequential scanning scheme. Referring to FIG. 4, in 401, an X-ray tube is controlled to irradiate an X-ray to an object in at least one viewpoint. In 402, at least one piece of projection information is generated by the X-ray irradiated to the object in the at least one viewpoint. In an example, in 402, first projection information may be generated as a result of an X-ray irradiated in a first viewpoint among the at least one viewpoint, and second projection information may be generated as a result of an X-ray irradiated in a second viewpoint among the at least one viewpoint. In this example, the first projection information and the second projection information are interpolated, and the predicted intermediate projection information is generated.

In 403, predicted intermediate projection information is compared with measured intermediate projection information from the generated projection information. The predicted intermediate projection information is predicted from pieces of projection information generated from different viewpoints. The measured intermediate projection information is measured in an intermediate viewpoint corresponding to the predicted intermediate projection information.

For example, predicted intermediate projection information, predicted from the first projection information and the second projection information, is compared with measured intermediate projection information measured in an intermediate viewpoint and corresponding to the predicted intermediate projection information.

In 404, the X-ray tube is controlled based on a result of operation 403. It is also determined whether the X-ray is to be irradiated in an additional viewpoint. In an example, when a correlation value between the predicted intermediate projection information and the measured intermediate projection information is determined to be greater than a predetermined reference in 403, at operation 404, it is determined that the X-ray is not required to be irradiated in the additional viewpoint. Operation 405 would then be performed. In other words, additional projection information are not measured, and instead pieces of additional projection information are combined using pieces of projection information that are already measured using an interpolation scheme. In this example, the generated projection information is reconstructed, and a 3D image representing the object is acquired in 405. In another example, when the correlation value is determined to be equal to or less than the predetermined reference in 403, additional projection information is measured through irradiation of an X-ray in an additional viewpoint. Accordingly, a control signal to irradiate an X-ray in an additional viewpoint is generated, and irradiation of the X-ray is controlled.

In other words, in the image reconstruction method of FIG. 4, when a difference between the predicted intermediate projection information and the measured intermediate projection information is greater than a predetermined reference, as the result of operation 403, the X-ray may be controlled to be irradiated in the additional viewpoint so that additional projection information is generated. The X-ray is irradiated in the additional viewpoint in 401, and additional projection information is generated in 402. It is to be understood that in the embodiment of the present invention, the operations in FIG. 4 are performed in the sequence and manner as shown although the order of some steps and the like may be changed without departing from the spirit and scope of the present invention. In accordance with an illustrative example, a computer program embodied on a non-transitory computer-readable medium may also be provided, encoding instructions to perform at least the method described in FIG. 4.

The image reconstruction method using the non-sequential scanning scheme, according to the above-described examples may be recorded, stored, or fixed in one or more non-transitory computer-readable media that includes program instructions to be implemented by a computer to cause a processor to execute or perform the program instructions. The media may also include, alone or in combination with the program instructions, data files, data structures, and the like. The program instructions recorded on the media may be those specially designed and constructed, or they may be of the kind well-known and available to those having skill in the computer software arts. Examples of non-transitory computer-readable media include magnetic media such as hard disks, floppy disks, and magnetic tape; optical media such as CD ROM disks and DVDs; magneto-optical media such as optical discs; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules in order to perform the operations and methods described above, or vice versa.

According to embodiments, an optimal scan path may be set by using, as feedback information, a relationship between pieces of neighboring projection information acquired in real time, instead of using an existing sequential scanning scheme, and thus it is possible to minimize a total dose of an X-ray.

Additionally, according to embodiments, a system may be enabled to recognize, in real-time, and to select information of a scan view required for reconstruction through a non-sequential scanning scheme, and thus it is possible to obtain an optimal reconstruction result.

A computing system or a computer may include a microprocessor that is electrically connected with a bus, a user interface, and a memory controller. It may further include a flash memory device. The flash memory device may store N-bit data via the memory controller. The N-bit data is processed or will be processed by the microprocessor and N may be 1 or an integer greater than 1. Where the computing system or computer is a mobile apparatus, a battery may be additionally provided to supply operation voltage of the computing system or computer. It will be apparent to those of ordinary skill in the art that the computing system or computer may further include an application chipset, a camera image processor (CIS), a mobile Dynamic Random Access Memory (DRAM), and the like. The memory controller and the flash memory device may constitute a solid state drive/disk (SSD) that uses a non-volatile memory to store data.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An image reconstruction system employing a non-sequential scanning scheme, the image reconstruction system comprising:
    a projection information generating unit configured to generate a piece of projection information by an X-ray irradiated to an object in a viewpoint;
    a projection information comparing unit configured to compare predicted intermediate projection information with measured intermediate projection information from the generated projection information, wherein the predicted intermediate projection information is predicted from pieces of projection information generated from different viewpoints, and the measured intermediate projection information is measured in an intermediate viewpoint corresponding to the predicted intermediate projection information;
    a determining unit configured to determine whether to irradiate the X-ray to the object in an additional viewpoint based on a result of the comparing; and
    an image reconstructing unit configured to reconstruct the generated projection information, and to acquire an image representing the object.

2. The image reconstruction system of claim 1, wherein the projection information generating unit is further configured to generate first projection information based on an X-ray irradiated in a first viewpoint, and to generate second projection information based on an X-ray irradiated in a second viewpoint.

3. The image reconstruction system of claim 2, wherein the projection information comparing unit is further configured to compare predicted intermediate projection information predicted from the first projection information and the second projection information, with measured intermediate projection information measured in an intermediate viewpoint, which corresponds to the predicted intermediate projection information.

4. The image reconstruction system of claim 3, wherein the projection information generating unit is further configured to interpolate the first projection information and the second projection information, and to generate the predicted intermediate projection information.

5. The image reconstruction system of claim 2, wherein, when a difference between the predicted intermediate projection information and the measured intermediate projection information is equal to or less than a predetermined reference as the result of the comparing, the projection information generator is further configured to generate first additional projection information by interpolating the measured intermediate projection information and the first projection information, and to generate second additional projection information by interpolating the measured intermediate projection information and the second projection information, and
    wherein the image reconstructing unit is a three-dimensional (3D) image reconstructing unit.

6. The image reconstruction system of claim 1, further comprising:
    an X-ray irradiator configured to control an X-ray tube to irradiate the X-ray to the object in the viewpoint, wherein, when a difference between the predicted intermediate projection information and the measured intermediate projection information is greater than a predetermined reference, the X-ray irradiating unit is further configured to control the X-ray to be irradiated in the additional viewpoint to generate additional projection information.

7. The image reconstruction system of claim 1, wherein the non-sequential scanning scheme for an expected scan path is set in advance of the expected scan.

8. The image reconstruction system of claim 1, wherein the projection information comparing unit verifies a correlation value between the predicated intermediate projection information and the measured intermediate projection information.

9. An image reconstruction method using a non-sequential scanning scheme, the image reconstruction method comprising:
    generating at least one piece of projection information by an X-ray irradiated to an object in a viewpoint;
    comparing predicted intermediate projection information with measured intermediate projection information from the generated projection information, wherein the predicted intermediate projection information is predicted from pieces of projection information generated from different viewpoints, and the measured intermediate projection information is measured in an intermediate viewpoint corresponding to the predicted intermediate projection information;

determining whether to irradiate the X-ray to the object in an additional viewpoint based on a result of the comparing; and reconstructing the generated projection information, and acquiring an image representing the object, wherein the generating further comprises generating first projection information based on an X-ray irradiated in a first viewpoint, and generating second projection information based on an X-ray irradiated in a second viewpoint.

10. The image reconstruction method of claim 9, wherein the comparing further comprises comparing predicted intermediate projection information predicted from the first projection information and the second projection information, with measured intermediate projection information measured in an intermediate viewpoint corresponding to the predicted intermediate projection information.

11. The image reconstruction method of claim 9, wherein the generating further comprises interpolating the first projection information and the second projection information, and generating the predicted intermediate projection information.

12. The image reconstruction method of claim 9, wherein the controlling further comprises controlling the X-ray to be irradiated in the additional viewpoint so that additional projection information is generated, when a difference between the predicted intermediate projection information and the measured intermediate projection information is greater than a predetermined reference.

13. A computer program embodied on a non-transitory computer readable recording medium, the computer program configured to control a processor to perform the method of claim 9.

14. An image reconstruction apparatus using a non-sequential scanning scheme, the image reconstruction apparatus comprising:

a projection information generator configured to generate a piece of projection information using an X-ray irradiated to an object in a viewpoint;

a projection information comparator configured to compare predicted intermediate projection information and measured intermediate projection information from the generated projection information and outputting a result indicative thereof;

a determining processor configured to control the X-ray to be irradiated in an additional viewpoint to generate additional projection information when a difference between the predicted intermediate projection information and the measured intermediate projection information is greater than a predetermined reference; and an image processor configured to reconstruct the generated projection information to produce an image of the object.

15. The image reconstruction apparatus of claim 14, wherein the predicted intermediate projection information is predicted from pieces of projection information generated from different viewpoints, and wherein the measured intermediate projection information is measured in an intermediate viewpoint corresponding to the predicted intermediate projection information.

16. The image reconstruction apparatus of claim 14, further comprising:

an X-ray irradiator configured to control an X-ray tube to irradiate the X-ray to the object in the viewpoint, wherein, when a difference between the predicted intermediate projection information and the measured intermediate projection information is greater than a predetermined reference, the X-ray irradiating unit is further configured to control the X-ray to be irradiated in the additional viewpoint to generate additional projection information.

17. The image reconstruction apparatus of claim 14, wherein, when a difference between the predicted intermediate projection information and the measured intermediate projection information is equal to or less than a predetermined reference as the result of the comparing, the projection information generator is further configured to generate first additional projection information by interpolating the measured intermediate projection information and a first projection information, and to generate second additional projection information by interpolating the measured intermediate projection information and a second projection information.

18. An image reconstruction method using a non-sequential scanning scheme, the image reconstruction method comprising:

generating a piece of projection information using an X-ray irradiated to an object in a viewpoint;

comparing predicted intermediate projection information and measured intermediate projection information from the generated projection information and outputting a result indicative thereof;

controlling the X-ray to be irradiated in an additional viewpoint to generate additional projection information when a difference between the predicted intermediate projection information and the measured intermediate projection information is greater than a predetermined reference; and reconstructing the generated projection information to produce a three-dimensional (3D) image of the object.

19. The image reconstruction method of claim 18, wherein the comparing further comprises comparing predicted intermediate projection information predicted from the first projection information and the second projection information, with measured intermediate projection information measured in an intermediate viewpoint corresponding to the predicted intermediate projection information.

20. The image reconstruction method of claim 18, wherein the generating further comprises interpolating the first projection information and the second projection information, and generating the predicted intermediate projection information.

21. The image reconstruction method of claim 18, wherein the controlling further comprises controlling the X-ray to be irradiated in the additional viewpoint so that additional projection information is generated, when a difference between the predicted intermediate projection information and the measured intermediate projection information is greater than a predetermined reference.

22. A computer program embodied on a non-transitory computer readable recording medium, the computer program configured to control a processor to perform the method of claim 18.

* * * * *